United States Patent
Taylor et al.

(10) Patent No.: US 9,554,843 B2
(45) Date of Patent: Jan. 31, 2017

(54) ADAPTER AND METHOD FOR CONVERTING GAS-ENHANCED ELECTROSURGICAL COAGULATION INSTRUMENT FOR CUTTING

(75) Inventors: Kenneth D. Taylor, Broomfield, CO (US); Stephen N. Donnigan, Highlands Ranch, CO (US); Alan R. Lee, Littleton, CO (US)

(73) Assignee: CONMED CORPORATION, Utica, NY (US)

( * ) Notice: Subject to any disclaimer, the term of this patent is extended or adjusted under 35 U.S.C. 154(b) by 2093 days.

(21) Appl. No.: 11/515,966

(22) Filed: Sep. 1, 2006

(65) Prior Publication Data
US 2008/0058801 A1    Mar. 6, 2008

(51) Int. Cl.
*A61B 18/14* (2006.01)
*A61B 18/04* (2006.01)
*A61B 18/00* (2006.01)

(52) U.S. Cl.
CPC ......... *A61B 18/1402* (2013.01); *A61B 18/042* (2013.01); *A61B 2018/00589* (2013.01); *A61B 2018/00601* (2013.01); *A61B 2018/00607* (2013.01); *A61B 2018/00916* (2013.01)

(58) Field of Classification Search
CPC .............. A61B 18/042; A61B 18/1402; A61B 2018/00589; A61B 2018/00601; A61B 2018/00607; A61B 2018/00916
USPC ......................................... 606/40, 41, 49, 45
See application file for complete search history.

(56) References Cited

U.S. PATENT DOCUMENTS

| | | |
|---|---|---|
| 2,828,747 A | 4/1958 | August |
| 4,040,426 A | 8/1977 | Morrison, Jr. |
| 4,057,064 A | 11/1977 | Morrison, Jr. et al. |
| 4,060,088 A | 11/1977 | Morrison, Jr. et al. |
| 4,492,832 A | 1/1985 | Taylor |
| 4,562,838 A | 1/1986 | Walker |
| 4,781,175 A | 11/1988 | McGreevy et al. |
| 4,834,095 A | 5/1989 | Miller |
| 5,066,294 A | 11/1991 | Cosmescu |
| 5,088,997 A | 2/1992 | Delahuerga et al. |

(Continued)

FOREIGN PATENT DOCUMENTS

| | | |
|---|---|---|
| AU | 20071586 | 5/2002 |
| AU | 200071586 A1 | 5/2002 |

(Continued)

OTHER PUBLICATIONS

PCT International Search Report with attached Written Opinion of the International Searching Authority for International Application No. PCT/US2007/018622, dated Jun. 9, 2008, 13 pages.

(Continued)

*Primary Examiner* — Michael Peffley
*Assistant Examiner* — Samantha Good
(74) *Attorney, Agent, or Firm* — Frederick J. M. Price; Bond, Schoeneck & King, PLLC

(57) ABSTRACT

An adapter includes a coupling mechanism that mates with a protruding nozzle of a gas-enhanced electrosurgical coagulation handpiece to convert the coagulation handpiece into a gas-enhanced electrosurgical cutting instrument. An adapter electrode and flow passageways of the adapter conduct electrical energy and gas from the nozzle of the coagulation handpiece to a protruding cutting end portion of an adapter electrode.

21 Claims, 9 Drawing Sheets

(56) References Cited

U.S. PATENT DOCUMENTS

| | | | |
|---|---|---|---|
| 5,098,430 A | 3/1992 | Fleenor | |
| 5,108,389 A | 4/1992 | Cosmescu | |
| 5,114,422 A | 5/1992 | Cosmescu | |
| 5,160,334 A | 11/1992 | Billings et al. | |
| 5,186,714 A | 2/1993 | Boudreault et al. | |
| 5,195,958 A | 3/1993 | Phillips | |
| 5,199,944 A | 4/1993 | Cosmescu | |
| 5,207,675 A | 5/1993 | Canady | |
| 5,217,457 A | 6/1993 | Delahuerga et al. | |
| 5,244,462 A | 9/1993 | Delahuerga et al. | |
| 5,306,238 A | 4/1994 | Fleenor | |
| 5,312,397 A | 5/1994 | Cosmescu | |
| 5,318,516 A | 6/1994 | Cosmescu | |
| 5,320,621 A | 6/1994 | Gordon et al. | |
| RE34,780 E | 11/1994 | Trenconsky et al. | |
| 5,431,650 A | 7/1995 | Cosmescu | |
| 5,449,356 A | 9/1995 | Walbrink | |
| 5,496,315 A | 3/1996 | Weaver et al. | |
| 5,505,710 A | 4/1996 | Dorsey, III | |
| 5,531,743 A | 7/1996 | Nettekoven et al. | |
| 5,693,044 A | 12/1997 | Cosmescu | |
| 5,720,745 A | 2/1998 | Farin et al. | |
| 5,797,901 A | 8/1998 | Cosmescu | |
| 5,800,431 A | 9/1998 | Brown | |
| 5,836,909 A | 11/1998 | Cosmescu | |
| 5,836,944 A | 11/1998 | Cosmescu | |
| 5,951,548 A | 9/1999 | DeSisto et al. | |
| 6,039,736 A | 3/2000 | Platt, Jr. | |
| 6,090,107 A | 7/2000 | Borgmeier et al. | |
| 6,099,525 A | 8/2000 | Cosmescu | |
| 6,142,995 A | 11/2000 | Cosmescu | |
| 6,149,648 A | 11/2000 | Cosmescu | |
| 6,197,026 B1 | 3/2001 | Farin et al. | |
| 6,258,088 B1 | 7/2001 | Tzonev et al. | |
| 6,293,945 B1 | 9/2001 | Parins et al. | |
| 6,302,881 B1 | 10/2001 | Farin | |
| 6,328,736 B1 | 12/2001 | Mulier et al. | |
| 6,355,034 B2 | 3/2002 | Cosmescu | |
| 6,391,027 B1 | 5/2002 | Farin et al. | |
| 6,458,125 B1 * | 10/2002 | Cosmescu | 606/42 |
| 6,475,216 B2 | 11/2002 | Mulier et al. | |
| 6,602,249 B1 | 8/2003 | Stoddard et al. | |
| 6,635,034 B1 | 10/2003 | Cosmescu | |
| 6,702,812 B2 | 3/2004 | Cosmescu | |
| 6,716,211 B2 | 4/2004 | Mulier et al. | |
| 6,852,112 B2 | 2/2005 | Platt | |
| 6,911,029 B2 | 6/2005 | Platt | |
| 7,004,939 B2 | 2/2006 | Mackay | |
| 7,033,353 B2 | 4/2006 | Stoddard et al. | |
| 7,083,601 B1 | 8/2006 | Cosmescu | |
| 7,198,625 B1 | 4/2007 | Hui et al. | |
| 2001/0051804 A1 | 12/2001 | Mulier et al. | |
| 2003/0181904 A1 | 9/2003 | Levine et al. | |
| 2004/0044342 A1 * | 3/2004 | Mackay | 606/45 |
| 2004/0167512 A1 | 8/2004 | Stoddard et al. | |
| 2005/0113825 A1 | 5/2005 | Cosmescu | |

FOREIGN PATENT DOCUMENTS

| | | |
|---|---|---|
| CA | 2535467 A1 | 4/1993 |
| EP | 0545540 A1 | 6/1993 |
| EP | 1449487 A1 | 8/2004 |
| EP | 1561430 A1 | 8/2005 |
| EP | 1602338 A2 | 12/2005 |
| GB | 671497 | 5/1952 |
| GB | 1014995 | 11/1965 |
| GB | 1014995 | 12/1965 |
| GB | 1165148 | 9/1969 |
| GB | 2455037 | 4/2011 |
| WO | WO92/22258 A1 | 12/1992 |
| WO | 93/05721 A1 | 4/1993 |
| WO | WO98/14131 A1 | 4/1998 |
| WO | WO03/061499 A1 | 7/2003 |
| WO | 2006/084316 A1 | 8/2006 |
| WO | WO2007/129321 A2 | 11/2007 |

OTHER PUBLICATIONS

UK Search Report for Application No. GB0815571.5, dated Dec. 4, 2008, 2 pages.

Siemens, Electromedicine Compendium, publication, 1978, 6 pgs., Heinz Kresse—Publisher, Germany.

PCT International Preliminary Report on Patentability, dated Mar. 3, 2009, 8 pages.

* cited by examiner

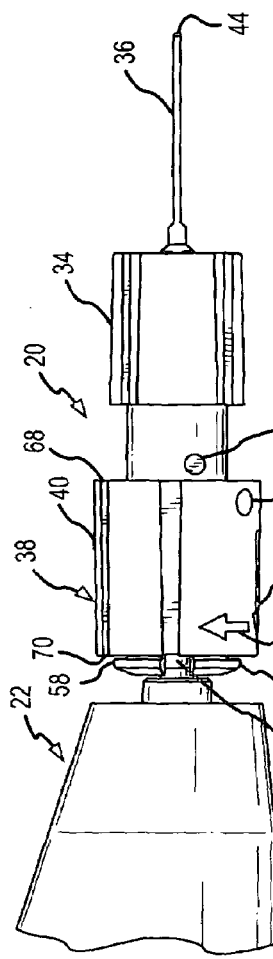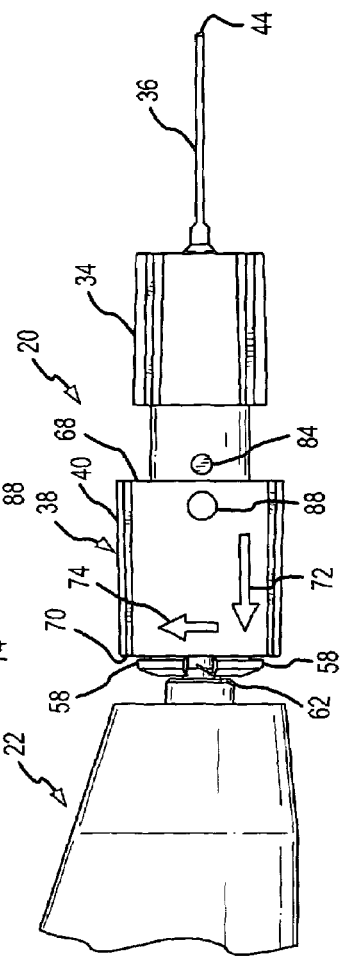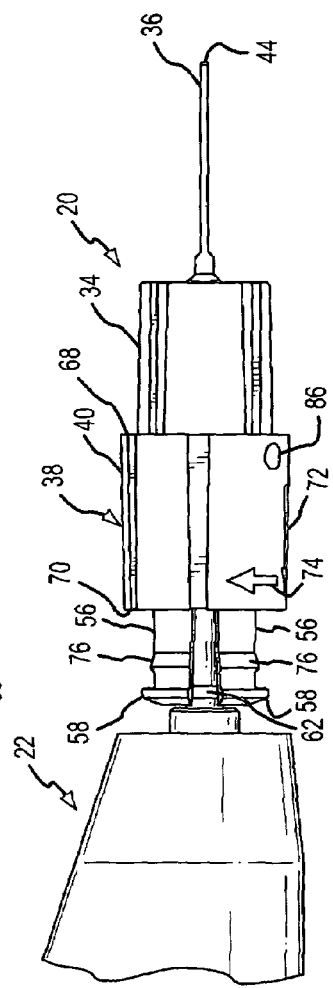
FIG.8
FIG.10
FIG.11

ADAPTER AND METHOD FOR CONVERTING GAS-ENHANCED ELECTROSURGICAL COAGULATION INSTRUMENT FOR CUTTING

This invention relates to electrosurgical instruments, and more specifically, to a new and improved adapter and method and apparatus for converting a gas-enhanced electrosurgical coagulation instrument into a cutting instrument which has a protruding blade electrode around which gas is delivered for electrosurgically cutting tissue.

BACKGROUND OF THE INVENTION

Gas-enhanced electrosurgery involves the delivery of electrical current in an ionized gas stream directed onto tissue to achieve an electrosurgical effect. Gas-enhanced electrosurgery was originally conceived to improve electrosurgical coagulation, or hemostasis, to stop blood from flowing from incised tissue. The principal US patent which describes gas-enhanced electrosurgical coagulation is U.S. Pat. No. 4,781,175. This patent describes a coagulation handpiece having a nozzle with an interior passageway through which the gas is directed in a flow stream or jet to the tissue. An electrode is recessed entirely within the nozzle to ionize the gas and to conduct the electrical energy in the flow stream to the tissue. The gas stream from the nozzle clears accumulated blood on the surface of the tissue and allows the electrical energy to interact directly with the tissue and create an eschar or seal on the surface of the tissue which prevents further bleeding from the tissue. The recessed position of the electrode within the nozzle avoids contacting the electrode with the tissue or the eschar in such a way to open the tissue to bleeding. The ionization and conductivity characteristics of the gas stream also enhances the energy distribution on the tissue to obtain superior hemostatic effects.

Other secondary benefits of gas-enhanced electrosurgical coagulation have been recognized. The gas, which is typically argon that is both chemically and physiologically inert, displaces the air which contains oxygen from the surgical site. The absence of oxygen at the surgical site minimizes any burning or charring effect of the electrical energy on the tissue. The absence or reduction of burned or charred tissue facilitates and increases normal physiological healing. The absence of oxygen also eliminates or substantially reduces smoke and pungent odors which are typical during conventional electrosurgery.

The minimization or elimination of burning, charring, smoke and odor have been recognized as desirable during electrosurgical cutting as well as during electrosurgical coagulation. Gas delivery to the tissue was then used during electrosurgical cutting. An instrument or handpiece that delivered gas during both coagulation and cutting is described in U.S. Pat. No. 5,088,997. The handpiece described in this patent uses a nose piece which concentrically surrounds a single electrosurgical electrode. The gas is delivered to the nose piece where it is distributed around the electrosurgical electrode. To achieve coagulation, the nose piece is moved longitudinally forward so that only a small amount of the distal tip of the electrode is exposed. To achieve cutting, the nose piece is moved longitudinally rearward to expose more of the distal tip of the electrosurgical electrode. Gas is delivered in both positions of the nose piece, and the distal tip of the electrode is exposed in both positions. Exposing more of the distal tip of the electrode is required when cutting tissue.

U.S. Pat. No. 5,098,430 describes a variation on a gas-enhanced cutting and coagulation handpiece. In this circumstance, a nozzle completely surrounds the electrode. For coagulation, the nozzle is moved to a forward position in which the distal tip of the electrode is completely recessed within the nozzle, in the same desirable manner as was described in U.S. Pat. No. 4,781,175. For cutting, the entire nozzle is moved backward to expose the distal tip of the electrode.

A further approach to the use of gas-enhanced electrosurgical coagulation with conventional electrosurgical cutting is described in U.S. Pat. No. 5,449,356. In this patent, a separate gas-enhanced electrosurgical coagulation device with a nozzle and a recessed active electrode is combined in a single instrument with a second active electrode that is used exclusively for electrosurgical cutting. No gas is delivered when the second active electrode is used to cut tissue. Instead, the tissue cutting proceeds in a still-air environment in the same manner as has been done for many previous decades in conventional electrosurgery. The second active electrode may be fixed in position, or the second active electrode may be made extendable and retractable to eliminate its presence from the surgical site during gas-enhanced electrosurgical coagulation. The primary benefit of this type of instrument is that the surgeon has both conventional electrosurgical cutting and gas-enhanced electrosurgical coagulation available from the same handpiece or instrument. The surgeon need only switch between the two different types of electrosurgical functionality when using the singular instrument.

Another approach to cutting tissue with the use of gas-enhanced electrosurgery is represented in U.S. Pat. No. 7,004,939 and Australian application AU 200071586, published May 16, 2002. The approach described in these documents is to entirely replace a nozzle assembly used on a multiple-use handpiece of the type described in U.S. Pat. No. 4,781,175. The typical nozzle assembly described in U.S. Pat. No. 4,781,175 includes a housing which defines the nozzle and which supports an electrosurgical electrode at a position recessed within the nozzle. U.S. Pat. No. 7,004,939 and the Australian application simply replace the nozzle assembly with the recessed electrode with a different nozzle assembly in which the distal tip of the electrode protrudes for cutting. This approach requires that a multiple-use, reusable handpiece be employed. One of the features of a multiple-use handpiece is that the nozzle assembly can be removed and replaced, as is necessary for sterilization and after many uses of the nozzle assembly. However, many surgeons and medical facilities prefer to use single-use electrosurgical handpieces. Single-use handpieces are supplied in a sterilized form in a sterile package, thereby eliminating the cost and risk associated with sterilizing multiple-use instruments prior to the procedure. After the procedure is completed, the single-use handpiece is simply disposed of. The cost of a multiple-use handpiece is so much greater than the cost of a disposable single-use handpiece that it may be more economical to use the disposable handpieces when the costs of labor for sterilizing the multiple-use handpiece and its components are considered.

SUMMARY OF THE INVENTION

The present invention is directed to an adapter which is conveniently connected to a protruding nozzle of a gas-enhanced electrosurgical coagulation handpiece to convert that coagulation handpiece into a gas-enhanced electrosurgical cutting device. The adapter is used with a disposable gas-enhanced electrosurgical coagulation handpiece, and therefore attains the cost advantages and other benefits associated with the use of a single-use disposable surgical instrument. The adapter itself may also be disposable. The connection of the adapter to the coagulation handpiece does not require disassembly of any aspect of the handpiece, and is rapidly and conveniently accomplished. Consequently, the adapter may be repeatedly connected to and disconnected from the coagulation handpiece during the course of a single surgical procedure, if desired. The benefits of gas-enhanced electrosurgical coagulation using a handpiece with a non-exposed or recessed active electrode within the nozzle are retained, while the benefits of gas-enhanced electrosurgical cutting with a protruding electrode are also obtained at relatively low cost and without using different or complex instruments.

In accordance with these and other aspects, the adapter includes a coupling mechanism which connects the adapter to the protruding nozzle of a gas-enhanced electrosurgical coagulation handpiece. The adapter includes a main body which supports an adapter electrode that is inserted into a flow passageway of the nozzle to contact a handpiece electrode when the adapter is connected to the nozzle, thereby conducting electrical energy to the adapter electrode. A distal end of the adapter electrode extends beyond the main body a sufficient distance to permit the electrical energy conducted through the adapter electrode to cut tissue. The main body includes at least one flow passageway that receives a stream of inert gas from an interior passageway of a nozzle and directs that flow of gas around the distal exposed end of the adapter electrode.

Another aspect of the invention relates to the gas-enhanced electrosurgical coagulation handpiece. The protruding nozzle of the coagulation handpiece includes a receiving retention structure, such as an annular groove, which is complementary to and connects with an adapter retention structure of the coupling mechanism. The receiving and adapter retention structures mate with each other to connect the adapter to the nozzle.

A further aspect of the invention includes a gas-enhanced electrosurgical cutting instrument formed by connecting a gas-enhanced electrosurgical coagulation handpiece and an adapter which has a protruding adapter electrode for cutting tissue.

Another aspect of the invention involves a method of converting a gas-enhanced electrosurgical coagulation handpiece into a cutting instrument. The method involves connecting an adapter to the protruding nozzle of the coagulation handpiece, contacting an adapter electrode of the adapter to a handpiece electrode within an interior passageway of the nozzle when the adapter is connected to the nozzle to conduct electrical energy from the handpiece electrode to a distal cutting end of the adapter electrode, and conducting substantially all of the gas from within the interior passageway of the nozzle into the flow passageway of the adapter and onto the distal cutting end of the adapter electrode.

A more complete appreciation of the present disclosure and its scope, and the manner in which it achieves the above and other improvements, can be obtained by reference to the following detailed description of presently preferred embodiments taken in connection with the accompanying drawings, which are briefly summarized below, and the appended claims.

BRIEF DESCRIPTION OF THE DRAWINGS

FIG. 8 is a side elevational view of the adapter shown in FIG. 7, with the collar in the clamping position.

FIG. 10 is a side elevational view of the adapter shown in FIG. 9, with the collar in a locking position.

FIG. 11 is a side elevational view of the adapter shown in FIG. 1, with the collar of the coupling mechanism in a disconnecting position.

DETAILED DESCRIPTION

Figure 1:
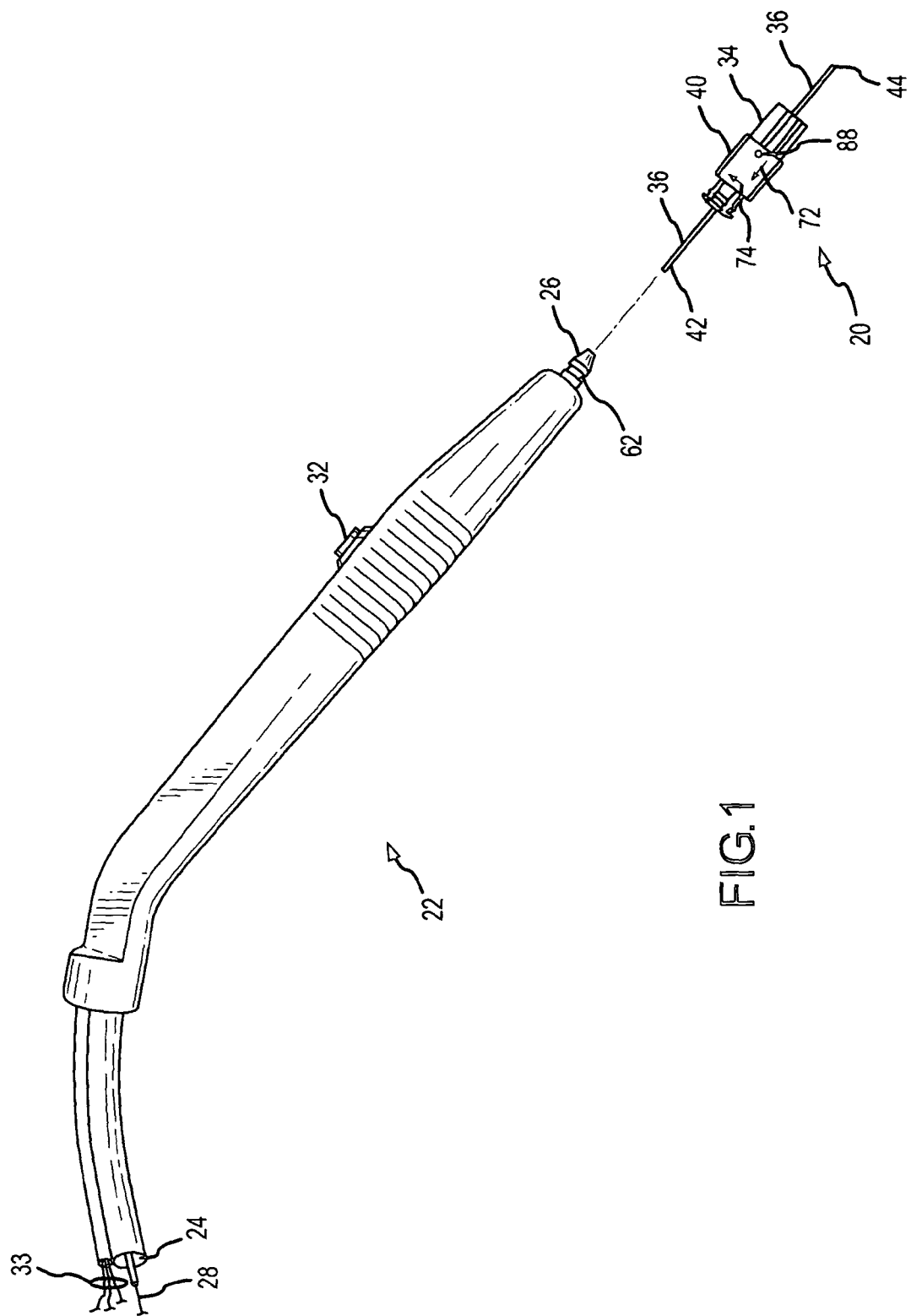
FIG. 1 is a perspective view of an adapter and a gas-enhanced electrosurgical coagulation handpiece which incorporate the present invention.
Figure 4:
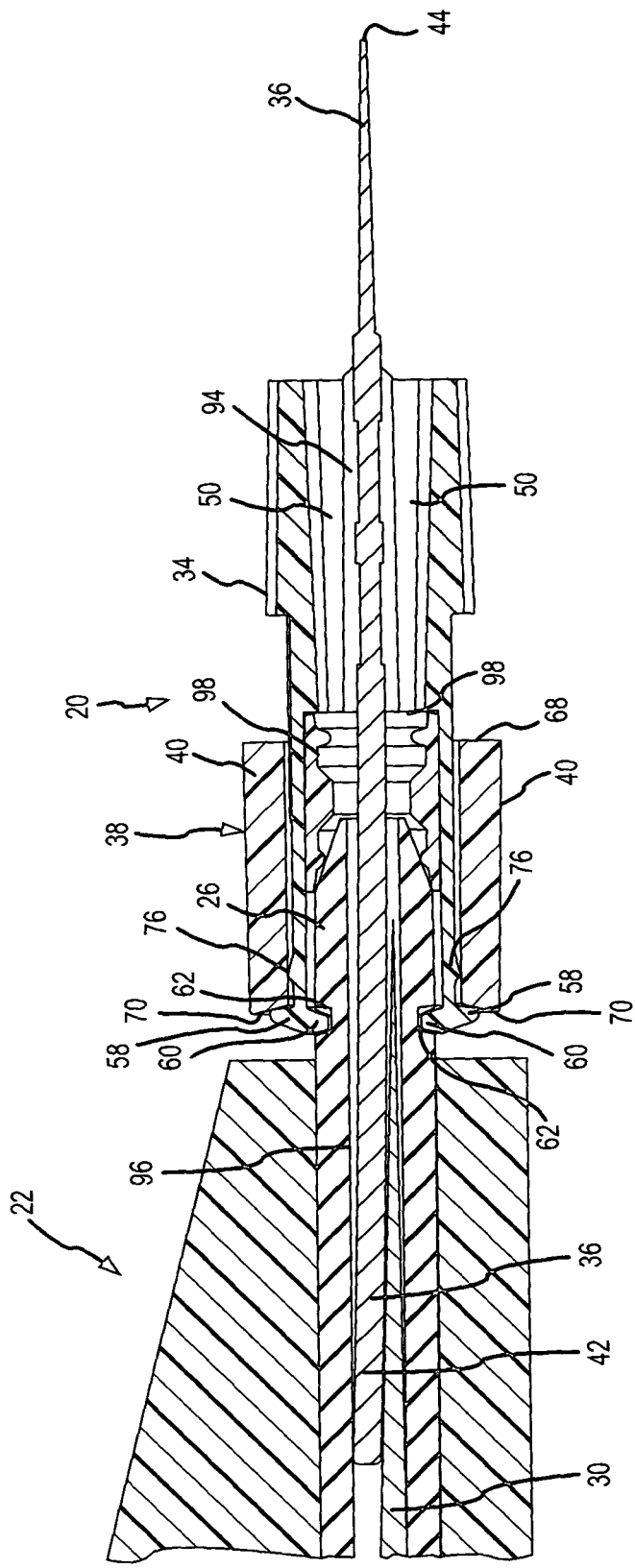
FIG. 4 is a longitudinal cross-sectional view of FIG. 3 taken substantially in the plane of line 4-4.

An adapter 20 for converting a preferably disposable, gas-enhanced electrosurgical coagulation handpiece 22 into a tissue cutting instrument or handpiece in accordance with the invention is shown FIG. 1. The handpiece 22 is connected by a hose or tube 24 to a conventional source of inert gas, for example argon gas, of a conventional gas-enhanced electrosurgical unit (not shown) used during electrosurgery. The gas is delivered through the tube 24 and is conducted internally within the handpiece 22 to a protruding hollow nozzle 26. The handpiece 22 is also connected by a conductor 28 to a conventional source of electrical energy of the conventional gas-enhanced electrosurgical unit which conducts electrical energy to a handpiece electrode 30 which is located within the nozzle 26, as shown in FIG. 4. The gas surrounds and flows along the electrode 30 within an internal passageway defined by the nozzle 26. In normal electrosurgical coagulation, the gas flowing in the nozzle 26 is ionized by the handpiece electrode 30 to conduct electrical current within a stream or jet of gas which flows from a distal end of the nozzle 26 to tissue (not shown) at the surgical site. The electrical energy in the stream of gas interacts with the tissue to coagulate blood flow or achieve hemostasis at the tissue. Because the electrode 30 does not protrude from the nozzle 26, it is not possible for the electrode 30 to contact the tissue and create a cutting effect. Indeed, the intended use of the coagulation handpiece 22 is to avoid cutting by preventing contact of the electrode 30 with the tissue. A button 32 operates a control switch (not shown) in the handpiece 22 to send signals to the electrosurgical unit through conductors 33, and thereby control the flow of electrosurgical energy and gas to the handpiece 22.

Figure 2:
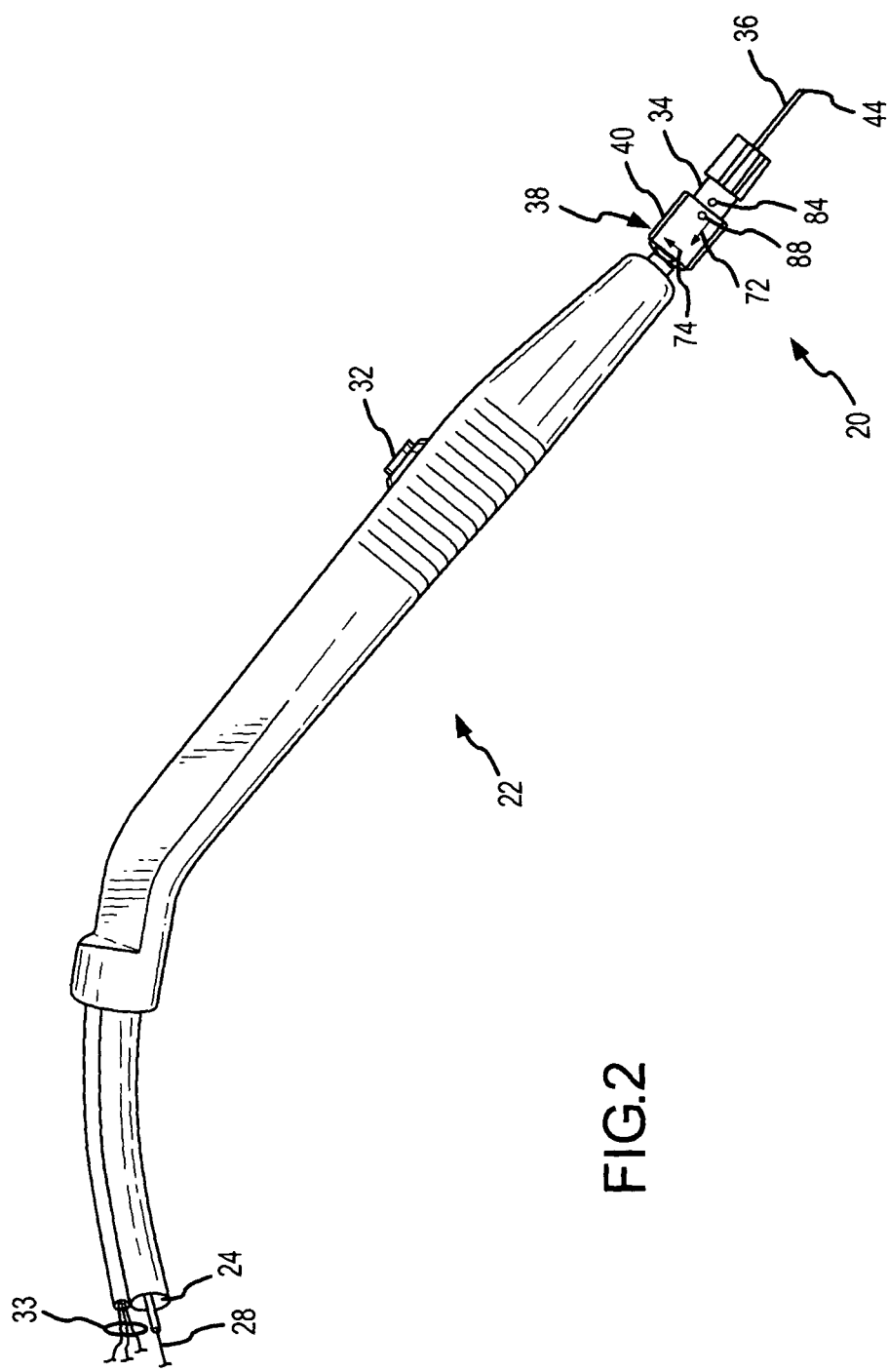
FIG. 2 is a perspective view similar to FIG. 1, showing the connection of the adapter to the gas-enhanced electrosurgical coagulation handpiece.
Figure 3:
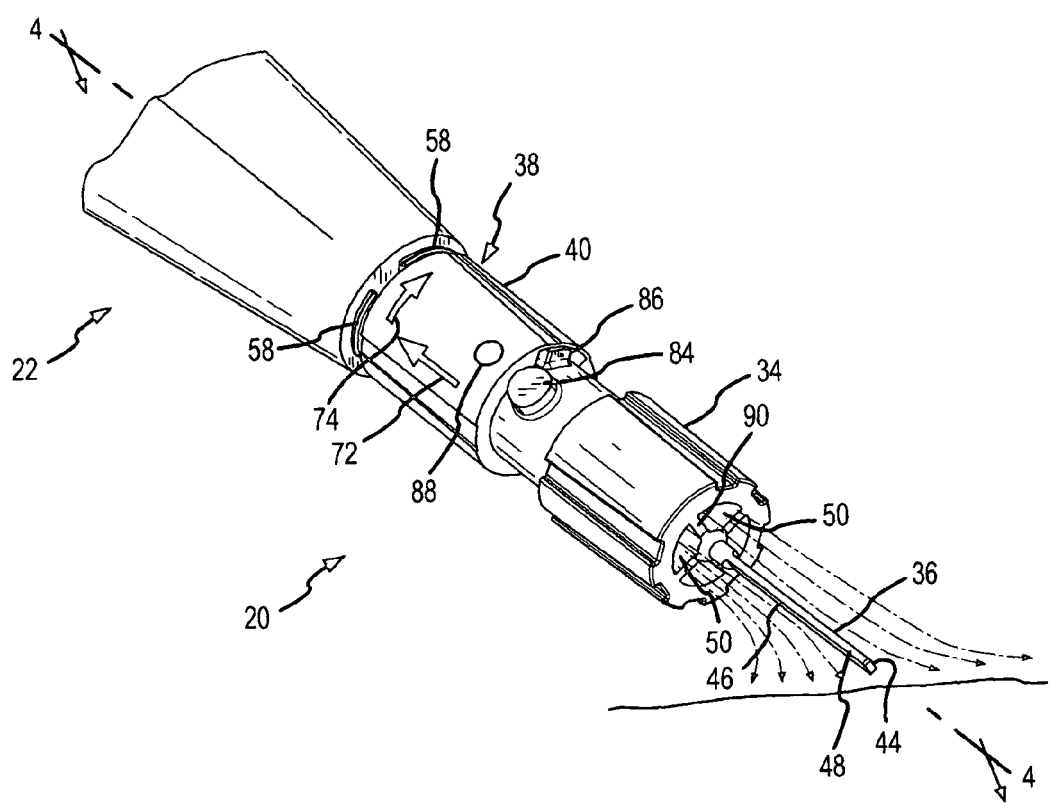
FIG. 3 is an enlarged perspective view of the adapter connected to an end of the gas-enhanced electrosurgical handpiece shown in FIG. 2.

The adapter 20 is selectively connectable to the protruding nozzle 26, as shown in FIGS. 2-4. Connecting the adapter 20 to the nozzle 26 converts the coagulation handpiece 22 into a gas-enhanced tissue cutting instrument. The adapter 20 comprises a main body 34, an adapter electrode 36 which is supported by the main body 34 and which extends both proximately and distally from the main body 34, and a coupling mechanism 38 at the proximal end of the main body 34 which connects the main body securely to the protruding nozzle 26. The coupling mechanism 38 includes a collar 40 that moves longitudinally and rotationally to cause the coupling mechanism 38 to connect the adapter 20 securely to the protruding nozzle 26 and to allow selective disconnection of the adapter 20 from the nozzle 26.

With the adapter 20 attached to the handpiece 22, a proximal end portion 42 of the adapter electrode 36 contacts the handpiece electrode 30 within the nozzle 26, as shown in FIG. 4. The contact of the electrodes 30 and 36 conducts the electrical energy from the handpiece electrode 30 to the adapter electrode 36. A distal cutting end portion 44 of the adapter electrode 36 projects beyond the main body 34 and includes opposite flat surfaces 46 separated by a narrow edge 48. The electrical energy discharges principally from the narrow edge 48 and into the tissue to vaporize tissue cells and part the tissue at the narrow edge 48. The electrical energy causes the tissue to separate, rather than a mechanical cutting action from the narrow edge 48. The distal end portion 44 of the adapter electrode 36 may also take the form of a needle which has a generally cylindrical transverse cross-sectional shape.

A plurality of flow passageways 50 extend within the main body 34. The flow passageways 50 receive the gas conducted through the nozzle 26, channel the gas through the main body 34, and expel the gas at the distal end of the main body 34 around the distal cutting end portion 44 of the adapter electrode 36, as shown in FIG. 3. The gas discharged from the flow passageways 50 surrounds the distal cutting end portion 44 of the adapter electrode 36 and establishes an inert gas atmosphere at the tissue site where the cutting occurs. The inert gas atmosphere eliminates or reduces oxygen at the tissue cutting surgical site and may enhance the electrical transfer from the cutting end portion 44 into the tissue. The absence or reduction of oxygen at the electrosurgical site minimizes the amount of tissue burning, tissue charring, smoke and odor which typically result from applying electrosurgical energy to tissue, especially adipose tissue as may be encountered in a breast resection surgical procedure, for example.

In this manner, the adapter 20 converts the handpiece 22 into a gas-enhanced cutting instrument. The distal cutting end portion 44 of the adapter electrode 36 is manipulated by the surgeon grasping and manipulating the handpiece 22. The use of a separate gas-enhanced electrosurgical cutting instrument is not necessary, and it is not necessary to replace any part of the coagulation handpiece 22 to obtaining cutting functionality. Furthermore, the adapter 20 can be removed from and reconnected to the coagulation handpiece 22 when desired during the surgical procedure to cut tissue and coagulate bleeding from the tissue.

More details of the adapter 20 are described in conjunction with FIGS. 4-13. The proximal end of the main body 34 is formed generally as a tube 52, as may be understood from FIG. 6. A plurality of longitudinally extending slots 54 in the tube 52 divide the proximal end of the tube 52 into a plurality of proximally extending legs 56.

A leg stop 58 extends radially outward from a proximal end of each leg 56. A lip 60 extends radially inward from the proximal end of the leg 56 opposite of the leg stop 58. The adapter 20 is attached to the handpiece 22 by placing the tube 52 and legs 56 over the nozzle 26 until each lip 60 inserts into an annular retention groove 62 that extends circumferentially around the exterior of the nozzle 26 (FIGS. 1 and 4). In order for the coagulation handpiece 22 to accept and retain the adapter 20, the annular retention groove 62 must be formed in the exterior surface of the nozzle 26. The lip 60 is an example of an adapter retention structure of the adapter 20, and the annular retention groove 62 is an example of a receiving retention structure of the handpiece 22.

The collar 40 surrounds the tube 52 at the exterior of the legs 56. The collar 40 has a thickness that extends radially between an interior annular surface 64 and an exterior annular surface 66. The interior annular surface 64 has a slightly larger diameter than the exterior diameter of the tube 52 which defines the legs 56. Consequently, the collar 40 is able to move longitudinally and rotationally relative to the legs 56. The collar 40 has a longitudinal length which extends between a distal end 68 and a proximal end 70. Longitudinal and rotational movement of the collar 40 secures the adapter 20 to the nozzle 26, and longitudinal and rotational movement of the collar in the opposite directions releases the adapter 20 from the nozzle 26.

Figure 7:
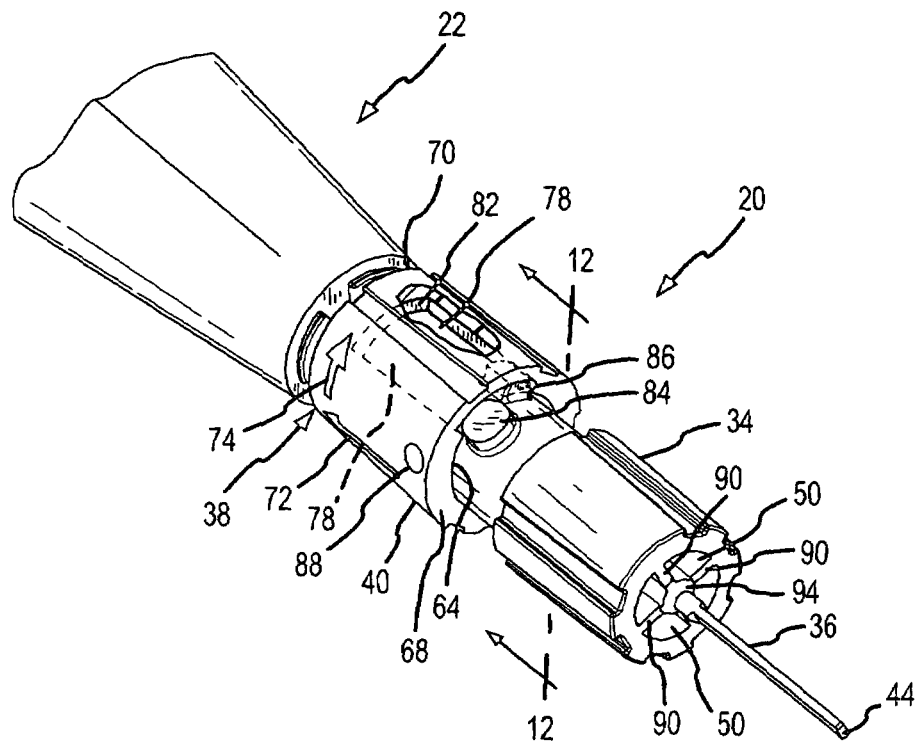
FIG. 7 is a perspective of the adapter similar to that shown in FIG. 3, with a portion of a collar broken away to illustrate features of a coupling mechanism of the adapter in a clamping position.

To secure the adapter 20 to the nozzle 26, the collar 40 is moved longitudinally in the proximal direction towards the proximal end of the legs 56, in the direction shown by a longitudinal movement indicia or arrow 72, to assume a clamping position illustrated in FIGS. 7 and 8. In the clamping position, the collar 40 applies inward transverse force on the legs 56 to thereby force and retain the lips 60 at the distal ends of the legs 56 in the groove 62 of the nozzle 26 (FIG. 4). A locking position is achieved when the collar 40 is rotationally moved from the clamping position (FIGS. 7 and 8) in the direction of a rotational movement indicia or arrow 74 to the locking position shown in FIGS. 2, 3, 5, 9 and 10. In the locking position, the collar 40 continues to apply the transverse force on the legs 56 to secure the lips 60 to the groove 62 on the nozzle 26. In addition however, rotation of the collar 40 into the locking position prevents the collar from moving longitudinally along the legs 56, thereby assuring that the adapter 20 will remain securely connected to the nozzle 26 of the coagulation handpiece 22. After the collar 40 is positioned into the locking position, the adapter 20 and the handpiece 22 are used as the cutting instrument. The indicia or arrows 72 and 74 are molded, printed, or otherwise formed in the exterior annular surface 66 of the collar 40.

To release the connection of the adapter 20 from the nozzle 26 of the handpiece 22, the collar 40 is rotated in the opposite direction of the rotational movement arrow 74, and then the collar 40 is moved longitudinally in the distal direction opposite of the longitudinal movement arrow 72. This movement positions the collar 40 in a disconnecting position shown in FIGS. 1 and 11. In the disconnecting position, the legs 56 are free to deflect slightly radially outward and allow the lips 60 to move out of the annular groove 62 in the nozzle 26 (FIG. 4). With the lips 60 out of the annular groove 62, the adapter 20 can be separated from the nozzle 26. Movement of the collar 40 to the disconnecting position also allows the lips 60 to move over the nozzle 26 and into the annular groove 62 when attaching the adapter 20 to the nozzle 26.

Figure 6:
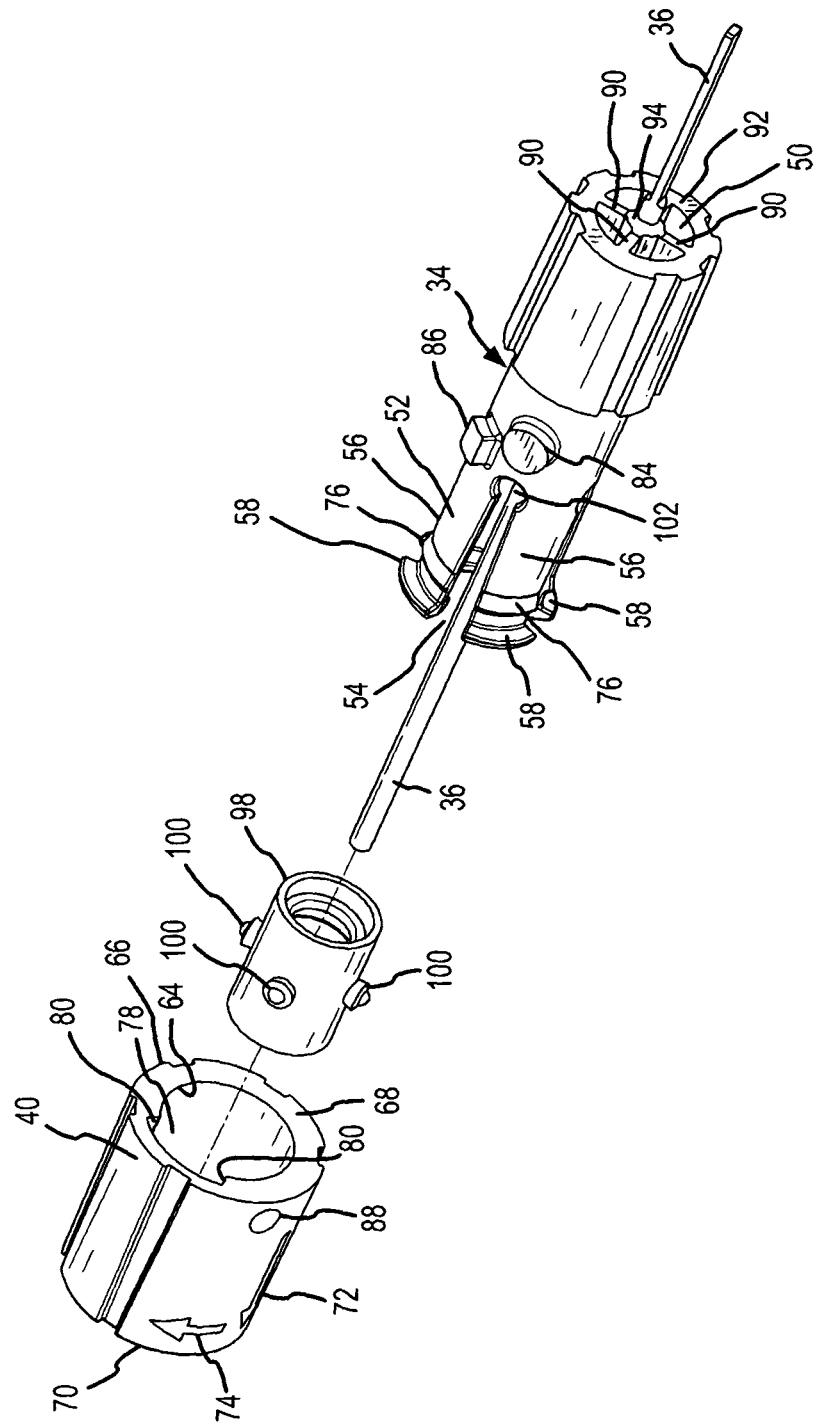
FIG. 6 is an exploded view of the adapter shown in FIG. 5.

The exterior surface of each of the legs 56 includes an external inclination 76 which protrudes outward from each of the legs 56, as shown in FIGS. 4 and 6. When the collar 40 is moved proximally to the clamping position, the interior annular surface 64 of the collar 40 rides up on the inclination 76 and forces the distal end of each of the legs 56 transversely inward in a cam-like manner. The transverse force on the distal end of the legs 56 forces the lips 60 into the annular groove 62 in the nozzle 26, thereby holding the adapter 20 to the nozzle 26.

The transverse force applied by the interior annular surface 64 riding up on the inclination 76 applies frictional force on the collar 40. The frictional force is sufficient to resist unintended rotational movement of the collar 40 out of the locking position. Consequently, the frictional force holds the collar 40 in the locking position. On the other hand, the frictional force on the collar 40 can be overcome from finger pressure applied to rotate the collar in the opposite direction from the locking position to the clamping position and to move the collar 40 distally toward the disconnecting position.

Figure 12:
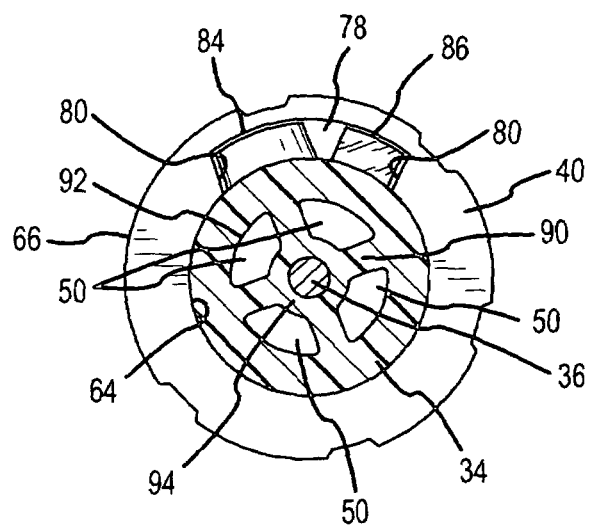
FIG. 12 is a transverse cross-sectional view of the adapter taken substantially in the plane of line 12-12 in FIG. 7.
Figure 9:
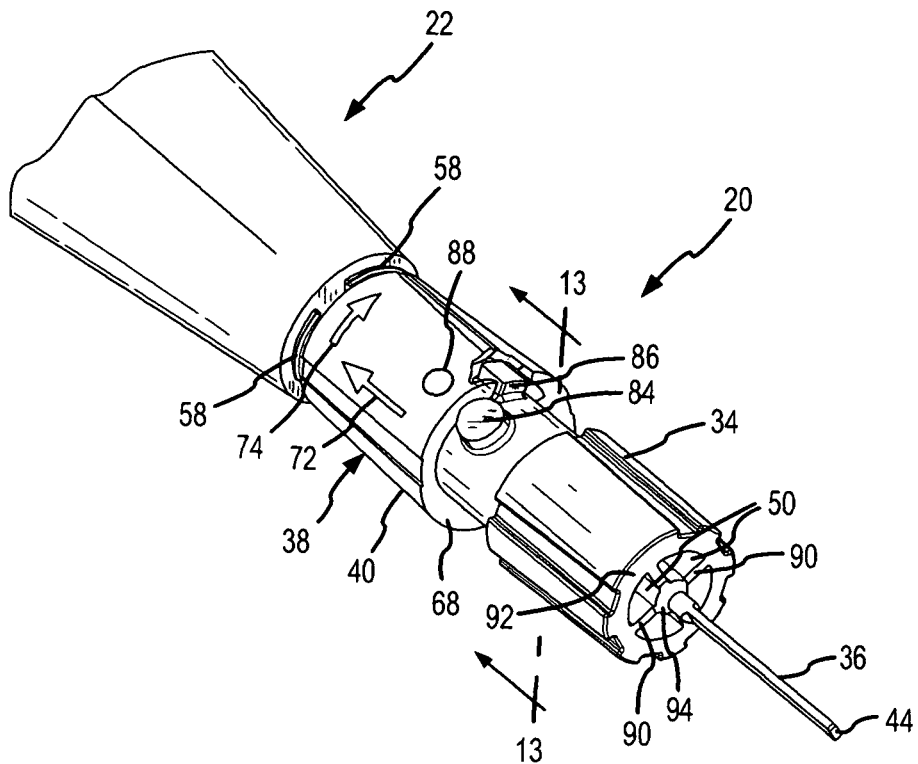
FIG. 9 is a perspective of the adapter similar to that shown in FIG. 7, with a portion of the collar broken away to illustrate features of the coupling mechanism of the adapter in a locking position.
Figure 13:
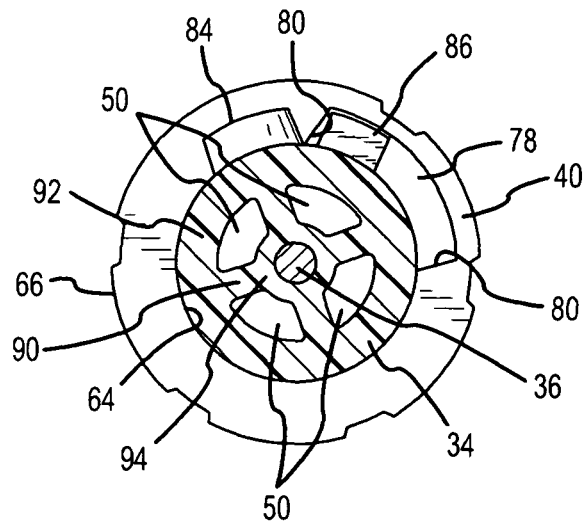
FIG. 13 is a transverse cross-sectional view of the adapter taken substantially in the plane of line 13-13 shown in FIG. 9.

The amount of longitudinal and rotational movement of the collar 40 is controlled by a rectangular groove 78 which is formed radially into the collar 40 from the interior annular surface 64, as shown in FIGS. 5-7, 12 and 13. The rectangular groove 78 commences at the distal end 68 of the collar 40 and extends longitudinally toward the proximal end 70 of the collar 40. The rectangular groove 78 has a circumferential width at the annular surface 64 between longitudinally extending sides 80 of the groove 78 (FIGS. 12 and 13). The rectangular groove 78 terminates at a proximal groove end surface 82 (FIG. 7) before reaching the proximal end 70 of the collar 40. The groove end surface 82 extends circumferentially between the distal ends of the longitudinally extending sides 80. The proximal groove end surface 82 is located distally relative to the proximal end 70 of the collar 40.

The tube 52 of the main body 34 includes a longitudinal stop 84 and a rotational stop 86 which interact with the rectangular groove 78 during rotational and longitudinal movement of the collar 40. The stops 84 and 86 protrude radially outward from the surface of the tube 52, as shown in FIGS. 5-7, 12 and 13. The rotational stop 86 is located closer to the proximal ends of the legs 56 than the longitudinal stop 84. The stops 84 and 86 are circumferentially spaced relative to one another to fit between the longitudinal sides 80 of the rectangular groove 78 (FIGS. 7 and 12). The circumferential spacing substantially limits rotational movement of the collar 40 by the contact of the stops 84 and 86 with the longitudinal sides 80. Consequently, the stops 84 and 86 prevent rotational movement of the collar 40 when both stops 84 and 86 are within the rectangular groove 78 but permit longitudinal movement of the collar 40 along the length of the legs 56 between the clamping and disconnecting positions. Both stops 84 and 86 are received within the rectangular groove 78 when the collar 40 is located in the disconnecting position.

Figure 5:
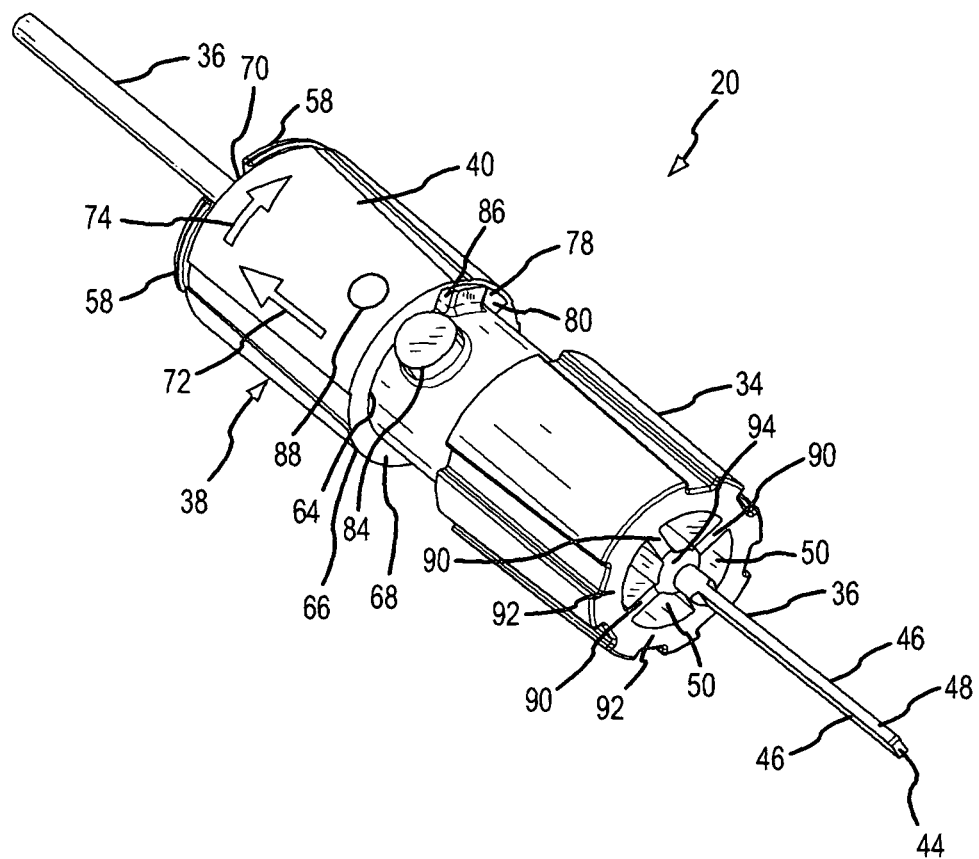
FIG. 5 is an enlarged perspective view of the adapter shown in FIG. 1.

Rotational movement of the collar 40 is possible once the collar 40 has been moved proximally to the clamping position. In the clamping position, the proximal end 70 of the collar 40 contacts the leg stops 58 which extend outward from the proximal ends of the legs 56 (FIGS. 5 and 8). In this clamping position, the longitudinal stop 84 is distally spaced beyond the distal end 68 of the collar 40, as shown in FIG. 8. Also, when in the clamping position, only the rotational stop 86 is located within the rectangular groove 78, thereby allowing the collar 40 to be rotated until the longitudinal sides 80 contact the rotational stop 86, as shown in FIGS. 5, 8, 9 and 13. In the locking position, further rotation by the collar 40 in the clockwise direction (as shown) is prevented by the contact between the longitudinal side 80 and the stop 86. The distal position of the longitudinal stop 84, being closely adjacent to the distal end 68 of the collar 40, prevents the collar 40 from moving longitudinally when the collar is rotated into the locking position, as shown in FIGS. 3, 5, 9 and 10. In the locking position, the proximal end 70 is adjacent to and confined by the leg stops 58, and the distal end 68 is adjacent to and confined by the longitudinal stop 84. In this locking position, the collar 40 possesses only one possible direction of motion, specifically rotational movement in the counterclockwise direction (as shown). All other directions of movement by the collar 40 are prevented through the interaction of the collar 40 with the stops 58, 84 and 86.

A locking indicia or dot 88 is molded, printed or otherwise formed on the exterior annular surface 66 of the collar in a position to be aligned with the longitudinal stop 84 when the collar 40 is in the locking position, as shown in FIGS. 3, 5, 9 and 10. The alignment of the locking dot 88 with the stop 84 indicates that the collar 40 is in the locking position. During surgical use, the collar 40 is in the locking position. In the clamping position of the collar 40, the locking dot 88 is circumferentially displaced from the stop 84, as shown in FIG. 8, to indicate that the locking position has not been achieved. The locking dot 88 is displaced slightly circumferentially relative to the rectangular groove 78 to provide this indication.

The flow passageways 50 within the interior of the main body 34 are defined by the plurality of ribs 90, as shown in FIGS. 3, 5-7, 9, 12 and 13. The ribs 90 extend radially inward from an outer continuous circumferential portion 92 of the main body 34 to converge into a center support tube 94. The support tube 94 is located approximately at the radial center of the main body 34 where it surrounds a portion of the adapter electrode 36. Preferably, the support tube 94 is molded around the adapter electrode 36. In this manner, the adapter electrode 36 is supported and secured by the main body 34. The convergence of the ribs 90 into the support tube 94 partitions the interior of the main body 34 into the plurality of flow passageways 50. The spaces between the ribs 90 define the flow passageways 50 through the main body.

Upon the insertion of the proximal end portion 42 of the adapter electrode 36 into the hollow nozzle 26, as shown in FIG. 4, the proximal end portion 42 contacts the handpiece electrode 30 and laterally displaces the handpiece electrode 30 from its normal center position in the nozzle 26. The thickness of the proximal end portion 42 of the adapter electrode 36 may be sufficient to also contact a side wall 96 of the interior passageway within the nozzle 26. Contacting the proximal end portion 42 with both the handpiece electrode 30 and the interior side wall 96 increases the contact force between the electrodes 30 and 36. Even though the proximal end portion 42 of the adapter electrode 36 and the handpiece electrode 30 may occupy substantially all of the space within the nozzle 26 on one radial side of the handpiece electrode 30, enough space within the interior of the nozzle 26 remains for the gas to flow around the contacting electrodes 30 and 36 and out of the nozzle 26.

A hollow interior seal 98 is located internally within the tube 52 of the main body 34, as shown in FIGS. 4 and 6. The seal 98 contacts the distal end of the nozzle 26 and confines the gas flowing from the distal end of the nozzle 26 into the flow passageways 50 within the main body 34. The internal seal 98 includes a plurality of seal stops 100 that extend radially outward from the seal 98 and into the slots 54 which divide the tube 52 into the legs 56. The stops 100 are located midway between the opposite longitudinal ends of the seal 98. When inserted into the tube 52, the internal seal 98 is moved until the seal stops 100 reach sockets 102 located at the distal termination of the slots 54. The sockets 102 retain the seal stops 100 and thereby hold the internal seal 98 in position.

With the internal seal 98 retained in position, the distal end of the internal seal 98 rests against the portion of the main body 34 which defines the flow passageways 50. When the adapter 20 is attached to the nozzle 26 (FIG. 4), the distal end of the nozzle 26 engages the proximal end of the internal seal 98 to form a gas-tight passageway from the interior of the nozzle 26 through the hollow interior of the seal 98 and into the passageways 50. The hollow interior of the internal seal 98, and the resilient material from which it is formed, such as silicone, thereby confines the flow of gas from the nozzle 26 into the flow passageways 50 of the main body 34 without leaks of the gas to the exterior.

The use of the adapter 20 and the conventional disposable coagulation handpiece 22 allows the surgeon to perform cutting and coagulation procedures during a gas-enhanced electrosurgical procedure by using only a single handpiece. The coupling mechanism 38 allows the adapter 20 to be removed and reattached as needed during the procedure. In this manner, both gas-enhanced electrosurgical cutting and coagulation capability are readily at the surgeon's disposal without the need to rely upon more costly or complex instruments or complicated procedures to change the functionality of a single instrument between cutting and coagulation capabilities. Moreover, if desired, electrosurgical coagulation may also be performed without disconnecting the adapter 20 from the handpiece 22.

The significance of these and other improvements and advantages will become apparent upon gaining a full appreciation of the ramifications and improvements of the present invention. A preferred embodiment of the invention and many of its improvements have been described with a degree of particularity. The description is of a preferred example of implementing the invention, and the detailed description is not necessarily intended to limit the scope of the invention. The scope of the invention is defined by the following claims.

The invention claimed:

1. An adapter to convert a gas-enhanced electrosurgical coagulation handpiece into a cutting instrument, the coagulation handpiece including a protruding hollow nozzle having an exterior surface and an interior passageway through which a stream of gas flows to tissue at a surgical site from a distal end of the nozzle, the coagulation handpiece also including a handpiece electrode within the interior passageway of the nozzle and from which electrical energy is conducted into the gas stream flowing from the distal end of the nozzle to the surgical site during gas enhanced electrosurgical coagulation, the adapter comprising:

a main body having a proximal end and a distal end, the proximal end of the main body formed generally as a tube within which to receive the distal end of the nozzle of the coagulation handpiece, wherein the tube includes a plurality of longitudinally extending slots which divide the tube into a plurality of longitudinally extending legs, the main body also including a coupling mechanism to secure the tube to the external surface of the protruding nozzle of the coagulation handpiece and thereby secure the adapter to the nozzle, wherein the coupling mechanism includes the plurality of legs and a collar which surrounds at least some portion of the plurality of legs to apply inward transverse force against the legs while in contact with the exterior surface of the nozzle to secure the adapter to the nozzle, the main body further including at least one flow passageway for conducting substantially all of the gas stream entering the tube from the interior passageway of the nozzle through the main body to the distal end of the main body when the distal end of the nozzle is received in the tube and the tube is secured to the external surface of the nozzle by the coupling mechanism;

an adapter electrode supported by the main body, the adapter electrode extending longitudinally through the main body, the adapter electrode including a proximal end portion within the tube and a distal cutting end portion which extends distally beyond the main body, the proximal end portion of the adapter electrode extending into the interior passageway of the nozzle to contact the handpiece electrode when the distal end of the nozzle is received in the tube and the tube is secured to the external surface of the nozzle by the coupling mechanism, the contact of the adapter electrode with the handpiece electrode conducting electrical energy from the handpiece electrode to the adapter electrode, the distal cutting end portion of the adapter electrode transferring the electrical energy conducted from the adapter and handpiece electrode, and the distal cutting end portion of the adapter electrode located relative to the at least one flow passageway to be surrounded by gas flowing from the at least one flow passageway; and an internal seal located within the tube to contact the distal end of the nozzle to confine the gas flow from the internal passageway of the nozzle into the at least one flow passageway of the main body when the distal end of the nozzle is received in the tube and the adapter is secured to the nozzle.

2. An adapter as defined in claim 1, wherein:

the collar is longitudinally movable along the plurality of legs; and longitudinal movement of the collar to a clamping position at the proximal end of the main body applies the inward transverse force to the legs and from the legs against the external surface of the nozzle to secure the adapter to the nozzle.

3. An adapter as defined in claim 2, wherein:

the collar is rotationally movable around the plurality of legs; and rotational movement of the collar around the proximal end of the main body from the clamping position to a locking position substantially prevents longitudinal movement by the collar to retain the inward transverse force from the legs against the external surface of the nozzle.

4. An adapter as defined in claim 3, wherein:

the main body includes a rotational stop and a longitudinal stop which both extend transversely outward from the tube, the rotational stop is located closer to the proximal end of the main body than the longitudinal stop; and the collar includes a groove formed adjacent to the legs which receives the rotational and longitudinal stops to confine the collar to longitudinal movement into the clamping position and to confine the collar into rotational movement from the clamping position to the locking position.

5. An adapter as defined in claim 1, wherein: the internal seal is annular.

6. An adapter as defined in claim 5, wherein:
at least one of the slots includes a socket;
the internal seal includes at least one seal stop that protrudes outward from the internal seal; and
the seal stop is positioned within the socket to retain the internal seal within the tube.

7. An adapter as defined in claim 6, wherein:
the main body includes a continuous internal circumferential portion and a plurality of ribs that extend radially inward from the circumferential portion, the plurality of ribs position the adapter electrode near the center of the main body, the continuous circumferential portion and the plurality of ribs create the at least one flow passageway within the main body.

8. An electrosurgical cutting device as defined in claim 1, wherein:
the proximal end of the adapter electrode is of sufficient size to contact the nozzle within the interior passageway.

9. A gas-enhanced electrosurgical coagulation handpiece for use with an adapter that converts the coagulation handpiece into a cutting instrument, the coagulation handpiece comprising a protruding hollow nozzle with an exterior surface and an interior passageway for conducting a stream of gas out of a distal end of the nozzle to tissue at a surgical site, the coagulation handpiece further comprising a handpiece electrode within the interior passageway of the nozzle from which electrical energy is conducted to the stream of gas conducted out of the distal end of the nozzle during gas-enhanced electrosurgical coagulation, the adapter comprising a main body supporting an adapter electrode which has a proximal end portion and a distal end cutting portion that extends distally beyond the main body, the main body also defining at least one flow passageway for receiving a gas stream and conducting the gas stream onto the distal end cutting portion of the adapter electrode, the main body also including an adapter retention structure to secure the adapter to the exterior surface of the nozzle, and the coagulation handpiece further comprising:
a receiving retention structure formed on the exterior surface of the protruding nozzle to complement and mate with the adapter retention structure to secure the adapter to the external surface of the nozzle with the proximal portion of the adapter electrode contacting the handpiece electrode and with the at least one flow passageway receiving gas conducted from the interior passageway of the nozzle.

10. A gas-enhanced electrosurgical coagulation handpiece as defined in claim 9, wherein:
the receiving retention structure is an annular groove located on the exterior of the nozzle; and
the adapter retention structure comprises a lip for extending into the annular groove and securing the adapter to the nozzle.

11. A gas-enhanced electrosurgical coagulation handpiece as defined in claim 9, further comprising:
a tube formed on a proximal end of the main body, the tube including a plurality of longitudinally extending slots which divide the tube into a plurality of longitudinally extending legs; and
a coupling mechanism which includes the plurality of legs and a collar which surrounds at least some portion of the plurality of legs on the exterior of the proximal end of the main body; and wherein:
the adapter retention structure is formed on an interior surface of at least one of the plurality of legs.

12. A gas-enhanced electrosurgical coagulation handpiece as defined in claim 11, wherein:
the collar is longitudinally movable along the plurality of legs; and
longitudinal movement of the collar to a clamping position at the proximal end of the main body applies an inward transverse force against the legs while in contact with the exterior surface of the nozzle force the adapter retention structure into engagement with the receiving retention structure and thereby secure the adapter to the nozzle.

13. A gas-enhanced electrosurgical coagulation handpiece as defined in claim 12, wherein:
the collar is rotationally movable around the plurality of legs; and
rotational movement of the collar around the proximal end of the main body from the clamping position to a locking position substantially prevents longitudinal movement by the collar to retain the inward transverse force from the legs while in contact with the exterior surface of the nozzle.

14. A gas-enhanced electrosurgical coagulation handpiece as defined in claim 13, wherein:
the main body includes a rotational stop and a longitudinal stop which both extend transversely outward from the tube, the rotational stop is located closer to the proximal end of the main body than the longitudinal stop; and
the collar includes a groove formed adjacent to the legs which receives the rotational and longitudinal stops to confine the collar to longitudinal movement into the clamping position and to confine the collar into rotational movement from the clamping position to the locking position.

15. A gas-enhanced electrosurgical coagulation handpiece as defined in claim 11, further comprising:
an internal seal located within the tube to contact the distal end of the nozzle to confine the gas flow from the internal passageway of the nozzle into the at least one flow passageway of the main body when the adapter is secured to the nozzle.

16. An electrosurgical cutting instrument for cutting tissue during an electrosurgical procedure, comprising:
a gas-enhanced electrosurgical coagulation handpiece which comprises a protruding nozzle having an exterior surface and an interior passageway through which a stream of gas flows to tissue at a surgical site from a distal end of the nozzle, the coagulation handpiece also including a handpiece electrode within the interior passageway from which electrical energy is conducted into the gas stream flowing from the distal end of the nozzle to the surgical site during gas-enhanced electrosurgical coagulation; and
an adapter which comprises a main body having a coupling mechanism to secure the main body to the exterior surface of the protruding nozzle and thereby secure the adapter to the nozzle, the main body supporting an adapter electrode which extends longitudinally through the main body from a proximal end within the coupling mechanism to a distal end which extends beyond the main body, the main body including at least one flow passageway for conducting substantially all of the gas stream from the interior passageway of the nozzle through the main body to the distal end of the adapter electrode when the main body is secured to the exterior surface of the nozzle by the coupling mechanism, the proximal end of the adapter electrode extending into the interior passageway of the nozzle to contact the handpiece electrode when the main body is secured to the exterior surface of the nozzle by the coupling mechanism, the contact of the adapter electrode with the handpiece electrode conducting electrical energy from the handpiece electrode to the adapter electrode, the distal end of the adapter electrode extending beyond the main body and located relative to the at least one flow passageway in the main body to be surrounded by gas flowing through the at least one flow passageway.

17. A method of converting a gas-enhanced electrosurgical coagulation handpiece into a cutting instrument, the coagulation handpiece including a protruding nozzle having an exterior surface and an interior passageway through which a stream of gas flows to tissue and a surgical site from a distal end of the nozzle, the coagulation handpiece also including a handpiece electrode located within the interior passageway to conduct electrical energy into the gas stream flowing from the nozzle to the surgical site during gas-enhanced electrosurgical coagulation, comprising:
  connecting an adapter to the exterior surface of the protruding nozzle, the adapter including an adapter electrode which extends longitudinally through the adapter to a distal cutting end and at least one flow passageway for conducting gas to the distal cutting end of the adapter electrode;
  contacting the adapter electrode to the handpiece electrode within the interior passageway of the nozzle when the adapter is connected to the exterior surface of the nozzle to conduct electrical energy from the handpiece electrode to the distal cutting end of the adapter electrode; and
  conducting substantially all of the gas from within the interior passageway of the nozzle into the at least one flow passageway of the adapter when the adapter is connected to the exterior surface of the nozzle.

18. A method as defined in claim 17, further comprising:
  performing electrosurgical cutting during a surgical procedure with the adapter connected to the exterior surface of the nozzle;
  disconnecting the adapter from the exterior surface of the nozzle during the surgical procedure; and
  performing electrosurgical coagulation during the surgical procedure using the handpiece when the adapter is disconnected from the nozzle.

19. A method as defined in claim 18, further comprising:
  reconnecting the adapter to the exterior surface of the nozzle during the surgical procedure after performing the electrosurgical coagulation; and
  again performing electrosurgical cutting during the surgical procedure with the adapter re-connected to the nozzle.

20. An adapter to convert a gas-enhanced electrosurgical coagulation handpiece into a cutting instrument, the coagulation handpiece including a protruding hollow nozzle having an exterior surface and an interior passageway through which a stream of gas flows to tissue at a surgical site from a distal end of the nozzle, the coagulation handpiece also including a handpiece electrode within the interior passageway of the nozzle and from which electrical energy is conducted into the gas stream flowing from the distal end of the nozzle to the surgical site during gas enhanced electrosurgical coagulation, the adapter comprising: a main body having a proximal end and a distal end, the proximal end of the main body formed generally as a tube within which to receive the distal end of the nozzle of the coagulation handpiece, wherein the tube includes a plurality of longitudinally extending slots which divide the tube into a plurality of longitudinally extending legs, the main body also including a coupling mechanism to secure the tube to the external surface of the protruding nozzle of the coagulation handpiece and thereby secure the adapter to the nozzle, wherein the coupling mechanism includes the plurality of legs and a collar which surrounds at least some portion of the plurality of legs to apply inward transverse force against the legs while in contact with the exterior surface of the nozzle to secure the adapter to the nozzle, the main body further including at least one flow passageway for conducting substantially all of the gas stream entering the tube from the interior passageway of the nozzle through the main body to the distal end of the main body when the distal end of the nozzle is received in the tube and the tube is secured to the external surface of the nozzle by the coupling mechanism; an adapter electrode supported by the main body, the adapter electrode extending longitudinally through the main body, the adapter electrode including a proximal end portion within the tube and a distal cutting end portion which extends distally beyond the main body, the proximal end portion of the adapter electrode extending into the interior passageway of the nozzle to contact the handpiece electrode when the distal end of the nozzle is received in the tube and the tube is secured to the external surface of the nozzle by the coupling mechanism, the contact of the adapter electrode with the handpiece electrode conducting electrical energy from the handpiece electrode to the adapter electrode, the distal cutting end portion of the adapter electrode transferring the electrical energy conducted from the adapter and handpiece electrode, and the distal cutting end portion of the adapter electrode located relative to the at least one flow passageway to be surrounded by gas flowing from the at least one flow passageway; wherein the external surface of the nozzle of the coagulation handpiece further includes a receiving retention structure; at least one of the legs includes an adapter retention structure formed on an interior surface of the one leg which interconnects with the receiving retention structure of the nozzle when the coupling mechanism secures the adapter to the nozzle; wherein the receiving retention structure of the nozzle comprises an annular groove formed in the exterior surface of the nozzle; and the adapter retention structure of the one leg comprises a lip which fits within the annular groove when the adapter is secured to the nozzle.

21. An adapter as defined in claim 20, wherein:
  the collar is longitudinally movable along the plurality of legs; and
  longitudinal movement of the collar to a clamping position at the proximal end of the main body applies an inward transverse force against the legs while in contact with the exterior surface to hold each lip in the annular groove.

* * * * *